United States Patent
Fojtik

(10) Patent No.: US 11,628,281 B2
(45) Date of Patent: Apr. 18, 2023

(54) EXOSKELETON DEVICES FOR USE WITH ELONGATED MEDICAL INSTRUMENTS

(71) Applicant: Transit Scientific, LLC, Park City, UT (US)

(72) Inventor: Shawn P. Fojtik, Park City, UT (US)

(73) Assignee: Transit Scientific, LLC, Salt Lake City, UT (US)

(*) Notice: Subject to any disclaimer, the term of this patent is extended or adjusted under 35 U.S.C. 154(b) by 0 days.

(21) Appl. No.: 15/260,202

(22) Filed: Sep. 8, 2016

(65) Prior Publication Data

US 2017/0065796 A1 Mar. 9, 2017

Related U.S. Application Data

(60) Provisional application No. 62/215,472, filed on Sep. 8, 2015.

(51) Int. Cl.
*A61M 25/10* (2013.01)
*A61M 29/02* (2006.01)
(Continued)

(52) U.S. Cl.
CPC ............ *A61M 25/104* (2013.01); *A61B 17/320725* (2013.01); *A61M 29/02* (2013.01);
(Continued)

(58) Field of Classification Search
CPC .... A61M 2025/1031; A61M 2025/105; A61M 2025/1056; A61M 2025/1086;
(Continued)

(56) References Cited

U.S. PATENT DOCUMENTS 5,441,515 A 8/1995 Khosravi et al.
5,562,620 A 10/1996 Klein et al.
(Continued)

FOREIGN PATENT DOCUMENTS

DE 100 17 147 A1 10/2001
JP HEI10-137257 A 5/1998
(Continued)

OTHER PUBLICATIONS

Definition of hypotube (Modern Grinding Jul. 5, 2018).*
(Continued)

*Primary Examiner* — Katherine H Schwiker
*Assistant Examiner* — Hong-Van N Trinh
(74) *Attorney, Agent, or Firm* — Dentons Durham Jones Pinegar

(57) ABSTRACT

An exoskeleton device is capable of being applied to an outer surface of an elongated medical instrument, such as a catheter or a balloon (e.g., an angioplasty balloon, etc.). The exoskeleton device includes a sleeve or another element that is configured to be placed over a distal portion of the elongated medical instrument, one or more features on the sleeve or other element for performing a procedure within the body of a subject, and one or more elements that communicate with the sleeve or other element and/or the features carried thereby to enable performance of the procedure within the body of the subject. Methods of applying exoskeleton devices to elongated medical instruments and methods of using exoskeleton devices are also disclosed.

16 Claims, 3 Drawing Sheets

(51) Int. Cl.
*A61B 17/3207* (2006.01)
*A61B 17/22* (2006.01)
*A61B 17/00* (2006.01)

(52) U.S. Cl.
CPC .............. *A61B 2017/00526* (2013.01); *A61B 2017/22061* (2013.01); *A61M 2025/109* (2013.01); *A61M 2025/1081* (2013.01); *A61M 2025/1084* (2013.01)

(58) Field of Classification Search
CPC .... A61M 2025/1088; A61M 2025/109; A61M 25/104; A61F 2/958; A61F 2002/9583; A61B 17/320725; A61B 2017/22061; A61B 2017/320733
See application file for complete search history.

(56) References Cited

U.S. PATENT DOCUMENTS

| | | | |
|---|---|---|---|
| 5,797,935 | A | 8/1998 | Baralh |
| 7,252,679 | B2 | 8/2007 | Fischell et al. |
| 8,518,101 | B2 | 8/2013 | Dreher |
| 9,114,031 | B2 | 8/2015 | Fulton |
| 9,277,935 | B2 | 3/2016 | Fulton |
| 2005/0080472 | A1 | 4/2005 | Atkinson et al. |
| 2005/0080478 | A1 | 4/2005 | Barongan |
| 2006/0259005 | A1* | 11/2006 | Konstantino ........... A61F 2/958 604/500 |
| 2006/0271093 | A1 | 11/2006 | Holman et al. |
| 2008/0044553 | A1* | 2/2008 | Freeman ................. A61L 2/07 427/2.24 |
| 2008/0221666 | A1 | 9/2008 | Licata et al. |
| 2010/0094392 | A1 | 4/2010 | Nguyen et al. |
| 2011/0152905 | A1* | 6/2011 | Eaton ..................... A61B 17/22 606/159 |
| 2011/0238154 | A1 | 9/2011 | Murphy et al. |
| 2013/0116655 | A1* | 5/2013 | Bacino ............ A61M 25/10184 604/509 |
| 2013/0138081 | A1 | 5/2013 | Stankus et al. |
| 2013/0144328 | A1* | 6/2013 | Weber ..................... A61F 2/958 606/200 |
| 2013/0204179 | A1 | 8/2013 | Konstantino et al. |
| 2014/0163594 | A1* | 6/2014 | Schur ............. A61B 17/320725 606/159 |
| 2015/0127034 | A1 | 5/2015 | Eaton |
| 2015/0157832 | A1* | 6/2015 | Moelgaard-Nielsen ..................... A61M 25/10 604/22 |
| 2015/0313732 | A1 | 11/2015 | Fulton |
| 2016/0067071 | A1* | 3/2016 | Jose ...................... A61L 31/005 623/1.15 |
| 2016/0135836 | A1 | 5/2016 | Fulton |

FOREIGN PATENT DOCUMENTS

| | | |
|---|---|---|
| JP | 2010-537680 A | 12/2010 |
| JP | 2014-528809 A | 10/2014 |
| JP | 2015-173913 A | 10/2015 |
| WO | 2009027531 A2 | 3/2009 |
| WO | 2013066566 A1 | 5/2013 |

OTHER PUBLICATIONS

International Search Report, International Patent Application No. PCT/US2016/050815, dated Dec. 1, 2016.
Written Opinion of the International Searching Authority, International Patent Application No. PCT/US2016/050815, dated Dec. 1, 2016.
European Patent Office, "Extended European search report," EPO Application No. 16845066.6, dated Mar. 15, 2019.
Japan Patent Office, Reasons for Rejection, Japanese Application No. 2018-531316, dated Feb. 26, 2019.
European Patent Office, Communication pursuant to Article 94(3) EPC, European Application No. 16845066.6, dated Mar. 18, 2020.
Japan Patent Office, Reasons for Rejection, Japanese Application No. 2019-201214, dated Dec. 22, 2020.
European Patent Office, "Communication pursuant to Article 94(3) EPC," European Application No. 16845066.6, dated Feb. 7, 2022.
Japan Patent Office, Decision of Rejection, Japanese Application No. 2019-201214, dated Oct. 19, 2021.
European Patent Office, "Communication pursuant to Article 94(3) EPC," European Application No. 16845066.6, dated Aug. 5, 2022.
Japan Patent Office, "Reasons for Rejection," Japanese Application No. 2019-201214, dated Aug. 18, 2022.

\* cited by examiner

EXOSKELETON DEVICES FOR USE WITH ELONGATED MEDICAL INSTRUMENTS

CROSS-REFERENCE TO RELATED APPLICATION

A claim for priority to the Sep. 8, 2015, filing date of U.S. Provisional Patent Application No. 62/215,472, titled EXOSKELETON DEVICES FOR USE WITH ELONGATED MEDICAL INSTRUMENTS ("the '472 Provisional Application") is hereby made pursuant to 35 U.S.C. § 119(e). The entire disclosure of the '472 Provisional Application is hereby incorporated herein.

TECHNICAL FIELD

This disclosure relates generally to exoskeleton devices for use on the outer surfaces of elongated medical instruments, such as catheters and balloons (e.g., angioplasty balloons, etc.). In particular, this disclosure relates to exoskeleton devices, such as devices for engaging or cutting into arterial plaques, infusion devices, electronic devices, shaping devices, etc., with tethers or other manipulation (e.g., removal, movement, etc.) features. This disclosure also relates to exoskeleton devices that include elongated elements on a body, or carrier, that may be applied to an elongated medical instrument, such as a catheter or an angioplasty balloon.

SUMMARY

In various aspects, this disclosure relates to exoskeleton devices that are configured to be disposed on elongated medical instruments, such as catheters or balloons (e.g., angioplasty balloons, etc.). Embodiments of exoskeleton devices that are configured for use with expandable elements of elongated medical instruments (e.g., balloons, such as angioplasty balloons; etc.) may also be configured to expand and resiliently contract when the expandable elements are respectively inflated and deflated. In addition to exoskeleton devices, assemblies that include an exoskeleton device and an elongated medical instrument (e.g., a catheter, a balloon, etc.) are disclosed, as are methods for using exoskeleton devices.

In one aspect, an exoskeleton device according to this disclosure may comprise a body, or a carrier, that is configured to be positioned over an elongated medical instrument, such as a catheter or an angioplasty balloon. The body may be defined by a single tubular element or by a plurality of elements. In addition, the body of an exoskeleton device configured for use with an expandable portion of an elongated medical instrument may, when the portion of the elongated medical instrument it surrounds expands radially (e.g., is inflated, etc.), also be configured to expand. The body of such an exoskeleton device may also be configured to resiliently return to its unexpanded configuration when the portion of the elongated medical instrument it surrounds contracts (e.g., is deflated, etc.). The body of an exoskeleton device according to this disclosure may also be configured to be used with elongated medical instruments of a plurality of different diameters.

In various embodiments, the body of an exoskeleton device may comprise a sleeve that is configured to completely surround the circumference of at least a portion of the length of an elongated medical instrument. A body with such a configuration may comprise an elongated tubular element, or a sleeve. The dimensions of the body, as well as the material from which it is made, may enable it to be positioned on an unexpanded portion of an elongated medical instrument and to remain on the unexpanded portion of the elongated medical instrument while that portion remains in an unexpanded (e.g., uninflated) state. Of course, in embodiments where the exoskeleton device is introduced onto an expandable portion of an elongated medical instrument, expansion of the expandable portion may cause the elongated medical instrument to further engage (or to be engaged by) the exoskeleton device.

In some embodiments, the body of an exoskeleton device may be configured to be circumferentially rolled upon itself, which may impart the carrier with the appearance of a ring. A body embodied in such a manner may be oriented adjacent to an end of an elongated medical instrument (e.g., a catheter or a balloon (e.g., an uninflated angioplasty balloon, etc.) prior to its introduction into the body of a subject, and then unrolled onto the elongated medical instrument, which may also occur prior to their introduction into the subject's body or while the elongated medical instrument and the exoskeleton device are being introduced into the subject's body.

As an alternative to including a single elongated tubular element, a body of an exoskeleton device according to this disclosure may comprise a plurality of collars that are configured to circumferentially surround and engage locations along the length of an elongated medical instrument, as well as one or more elongated elements that extend from one collar to another and, thus, that are configured to extend along at least a portion of a length of the elongated medical instrument. In embodiments where an exoskeleton device includes a plurality of elongated elements, the elongated elements may be configured for positioning at different radial positions around a surface of the elongated medical instrument. Together, the collars and the elongated element(s) define a cage for receiving at least a portion of the length of the elongated medical instrument.

The body of an exoskeleton device according to this disclosure may carry or comprise (e.g., ribs of a tubular embodiment, the elongated elements of a cage embodiment, etc.) exterior elements, which are configured to perform one or more specific functions when the exoskeleton device and the elongated medical instrument by which it is carried are introduced into the interior of a subject's body.

In a specific embodiment, the exterior elements may comprise small blades, which are known as "atherotomes." Such an exterior element may also be referred to herein as a "cutting element." An atherotome may include one or more edges. Exterior elements with atherotomes may, for example, be configured to cut into, score or otherwise engage a plaque into which they are forced (e.g., by inflation of the portion of the elongated medical instrument (e.g., the catheter, the angioplasty balloon, etc.) over which the atherotomes are positioned, etc.).

In embodiments where an atherotome resides on a catheter, the catheter may be forced against the plaque in such a way that the atherotome engages, scores and/or cuts into the plaque. In embodiments where the exoskeleton device resides on an angioplasty balloon, the atherotome may engage, score and/or cut into the plaque as the angioplasty balloon is expanded by inflating the angioplasty balloon.

In some embodiments, an atherotome may comprise a polymer that expands when placed under a load and that resiliently contracts when the load is released. More specifically, a width of the atherotome may expand when the atherotome is placed under tensile stress and resiliently contract when the tensile stress is released. Such a polymeric atherotome may include an edge that is more pronounced when little or no load is applied in a direction transverse to a length of the exterior element and that becomes less pronounced and, thus, loses some of its ability to cut into, score or otherwise engage the arterial plaque as more of a tensile load is applied to its opposite sides (e.g., as an angioplasty balloon on which the atherotome resides is inflated, etc.).

Alternatively, an exterior element that comprises an atherotome may be associated with the body of an exoskeleton device or, in embodiments where the external element comprises a part of the body, it may be associated with other elements of the body of the exoskeleton device in such a way that an orientation of the edge(s) of the atherotome changes as the body circumferentially extends or contracts. As an example, when the body is in a relaxed state, edge(s) of the exterior element may be oriented radially or substantially radially relative to a longitudinal axis of the exterior element. As the body circumferentially expands, the angle(s) at which the edge(s) of the exterior element is (are) oriented may become more tangential, thereby reducing the likelihood that the edge(s) will score, cut into or otherwise engage an arterial plaque.

Whether or not they comprise atherotomes, the exterior elements of an exoskeleton device according to this disclosure may include one or more conduits. An exterior element with a conduit extending therethrough may be configured to expel fluid, or cause fluid to be infused into the body of a subject, or to obtain a sample from the body of the subject. Some embodiments of exterior elements that include conduits (e.g., hypotubes, elongated tubular polymer elements, etc.) may include one or more small openings, which are referred to herein as "pores," that extend through a wall of the exterior element and that are positioned at an intermediate location along the length of the exterior element to enable fluid to flow from the conduits to the outer surface of the exterior element. Embodiments of exterior elements that include a plurality of pores may enable fluid delivery to a plurality of locations that are spread over a wide area. An exterior element that has a conduit may have an open distal end or one or more larger openings that extend through the wall of the exterior element to enable the delivery of fluid to a selected location within the body of a subject or the withdrawal of fluid from a selected location within the body of a subject.

Alternatively, the exterior elements of an exoskeleton device may comprise electrically conductive elements, such as circuit traces and electrodes. Electrically conductive elements may perform a variety of functions, including, without limitation, the delivery of heat to one or more desired locations within a subject's body and/or the delivery of electricity to one or more desired locations within a subject's body. Electrically conductive elements may also enable the communication of electrical signals to and/or from devices that are carried by an elongated medical instrument and by the body of an exoskeleton device to one or more desired locations within a subject's body (e.g., sensors, etc.).

Exterior elements that provide other types of functionality are also within the scope of this disclosure.

Some embodiments of exterior elements may be deformable, and configured to hold a shape into which they are formed, which may enable an exoskeleton device to define a shape of a portion of an elongated medical instrument (e.g., a catheter, an angioplasty balloon, etc.) on which the exoskeleton device resides.

An exoskeleton device according to this disclosure may optionally include a tether, which may extend proximally from the body of the exoskeleton device. The tether of an exoskeleton device may extend longitudinally (or at least somewhat longitudinally) from the body of the exoskeleton device. When the body of the exoskeleton device resides on an elongated medical instrument (e.g., a catheter. an angioplasty balloon, etc.) within the body of a subject, the exoskeleton device may extend in a proximal direction, to a location outside of the subject's body. Thus, the tether may have a length that exceeds the length of an elongated medical instrument with which the tether is used. Such a tether may be configured to ensure that the exoskeleton device can be removed from a subject's body, for example, when the catheter or the angioplasty balloon with which the exoskeleton device is associated is removed from the subject's body. In some embodiments, including those where one or more of the exterior elements of an exoskeleton device include conduits and pores or other openings, a tether may also include a conduit extending along its length. That conduit may communicate with the conduit of at least one exterior element, which enables fluid introduced into conduit of the tether to flow into the conduit of the at least one exterior element, to be communicated through the pores in the at least one exterior element, and to be introduced into a location where the at least one exterior element resides (e.g., into a blood vessel, into the presence of plaque within a blood vessel, etc.). In embodiments where electrical signals are to be conveyed to and/or from circuitry on an exoskeleton device, the tether may include or carry one or more wires.

In some embodiments, the tether may comprise a single elongated element, such as a wire, hypotube, elongated polymer element or the like. In other embodiments, an exoskeleton device may include two or more tethers. In embodiments that include a plurality of tethers, the tethers may remain separate from one another, or they may be secured together (e.g., by welding or bonding, by twisting, by braiding, etc.) along at least a portion of their lengths.

According to another aspect, methods for extending the functionality of an elongated medical instrument, such as a catheter or a balloon (e.g., an angioplasty balloon, etc.) are disclosed. Such a method may include installing an exoskeleton device onto an exterior of the elongated medical instrument (e.g., onto an exterior of a distal portion of the elongated medical instrument, etc.). With the exoskeleton device in place, the elongated medical instrument (e.g., its distal portion, etc.) may be introduced into a body of a subject. The elongated medical instrument (e.g., its distal portion, etc.) and the exoskeleton device carried thereby may then be advanced to a desired location with the subject's body. With the elongated medical instrument (e.g., its distal portion, etc.) and the exoskeleton device in place, one or both of them may be used to perform a procedure at the desired location within the subject's body. Thereafter, the elongated medical instrument and the exoskeleton device may be removed from the subject's body.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIGS. 1A, 1A-1, 2A and 3A show the embodiments of exoskeleton devices of FIGS. 1, 2 and 3, respectively, installed on elongated medical instruments;

FIGS. 1B, 1B-1, and 3B depict the elongated medical instruments of FIGS. 1A, 1A-1, and 3A, respectively—angioplasty balloons in the depicted embodiments—in expanded (e.g., inflated, etc.) states and the bodies of the exoskeleton devices of FIGS. 1 and 1A and of FIGS. 3 and 3A, respectively, in expanded states;

Similar reference characters in different drawings may refer to similar elements, which may, in some embodiments, include features, functions and/or other characteristics that are the same as or similar to one another.

DETAILED DESCRIPTION

Figure 1:
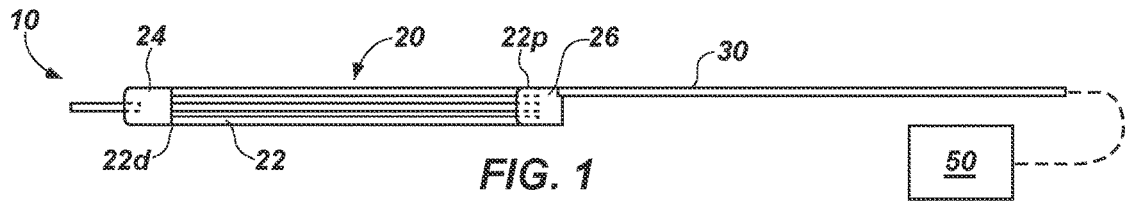
FIGS. 1, 2 and 3 illustrate various embodiments of exoskeleton devices, with each exoskeleton device including a body, or a carrier or cage, configured to surround an elongated medical instrument (e.g., a catheter, an angioplasty balloon, etc.), the body of the exoskeleton device being defined by a plurality of elongated external elements configured to be oriented along a length of the elongated medical instrument.
Figure 1A:
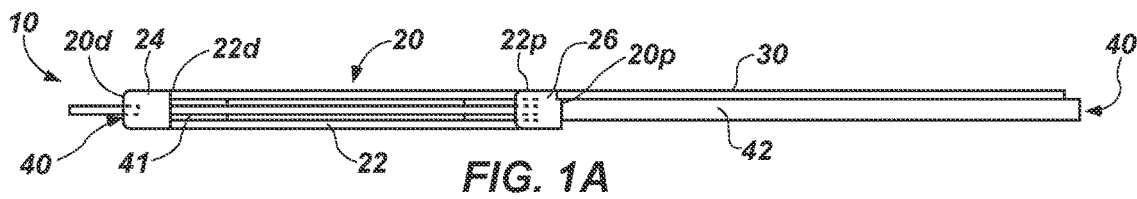
Figures 1, 1A, 1B:
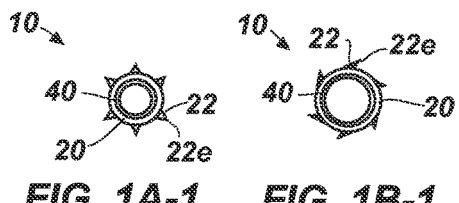
Figure 1B:
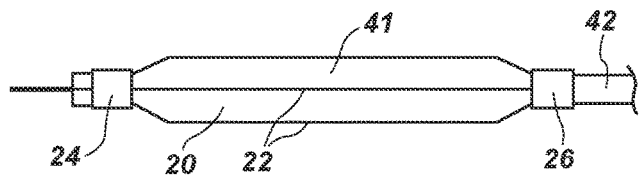

With reference to FIGS. 1-1B, an embodiment of an exoskeleton device 10 that is configured to be positioned over an angioplasty balloon (FIG. 1A) is depicted. The exoskeleton device 10 includes a body 20 and a tether 30.

The body 20 of the exoskeleton device 10 is defined by at least two collars—the distal collar 24 and the proximal collar 26 illustrated by FIGS. 1-1B—that are configured to be placed at different positions along the length of an elongated medical instrument 40 (FIGS. 1A and 1B), such as a catheter or a balloon (e.g., an angioplasty balloon, etc.), as well as one or more external elements 22 (a plurality of external elements 22 are shown in FIGS. 1-1B) that extend from the proximal collar 26 to the distal collar 24. The distal collar 24 and the proximal collar 26 may be configured to engage (e.g., resiliently, by interference fit, etc.) the elongated medical instrument 40 in a manner that holds the body 20 of the exoskeleton device 10 in place at a desired location along a length of the elongated medical instrument 40.

As depicted, the external elements 22 are elongate members that are oriented substantially parallel to one another. The external elements 22 may be arranged in such a way as to define an outer periphery of a receptacle (e.g., in a somewhat cylindrical fashion, etc.), such as a cage, for receiving an elongated medical instrument 40, such as a catheter or a balloon (e.g., an angioplasty balloon, etc.) (FIGS. 1A and 1B). While FIGS. 1-1B illustrate each external element 22 as being a substantially linear member that is oriented parallel to a length of the body 20, other orientations are also within the scope of this disclosure, including, without limitation, helically oriented external elements 22, external elements 22 with multiple curve (e.g., sigmoidal, or S, shapes, etc.), etc.

The distal collar 24 may be located at a distal end 20d of the body 20 of the exoskeleton device 10 and, in embodiments where the body 20 includes a plurality of external elements 22, may secure distal ends 22d of the external elements 22 in place relative to one another. The distal collar 24 may be configured to receive a distal end of an elongated medical instrument 40 and, thus, to hold the body 20, as well as the remainder of the exoskeleton device 10 in place on a distal portion 41 of the elongated medical instrument 40. In the depicted embodiment, with the exoskeleton device 10 in place on the distal portion 41 of the elongated medical instrument 40, a more proximal portion 42 of the elongated medical instrument 40 remains exposed.

The proximal collar 26 of the body 20 of the exoskeleton device 10 may be located at a proximal end 20p of the body 20. In embodiments where the body 20 includes a plurality of external elements 22, the proximal collar 26 may secure proximal ends 22p of the external elements 22 in place relative to one another. The proximal collar 26 may be configured to be positioned over, and to receive, a somewhat proximal portion 42 of the elongated medical instrument 40. In the embodiment illustrated by FIGS. 1-1B, the proximal collar 26 be positioned proximally adjacent to a proximal side of the distal portion 41 (e.g., an expandable element, etc.) of the elongated medical instrument 40. The proximal collar 26 may be configured to engage the portion of the elongated medical instrument 40 over which it is positioned and, thus, may hold the body 20 and the remainder of the exoskeleton device 10 in place on the distal portion 41 of the elongated medical instrument 40. As illustrated by FIG. 1B, the proximal collar 26, when positioned on the proximal side of an expandable distal portion 41 of an elongated medical instrument 40, may be configured to function in conjunction with the distal collar 24 to hold the body 20 in place over the distal portion 41, such as when the distal portion 41 is at least partially inflated, and may enable the body 20 of the exoskeleton device 10 to accommodate expansion of the distal portion 41.

In addition to a body 20, an exoskeleton device 10 according to this disclosure may include a tether 30. The tether 30 may be configured to enable an individual, such as a healthcare provider, to maintain control over the exoskeleton device 10 from a location outside of a subject's body while the exoskeleton device 10 and a distal portion 41 of an elongated medical instrument 40 on which the exoskeleton device 10 has been positioned remain within the subject's body. As an example, a tether 30 may enable an individual to remove the exoskeleton device 10 in the event that it becomes dislodged from the distal portion 41 of the elongated medical instrument 40. As another example, a tether 30 may facilitate removal of an elongated medical instrument 40 from a subject's body; for example, the tether 30 may be pulled with a proximal portion 42 of the elongated medical instrument 40 to reinforce or supplement a pulling force applied to the proximal portion 42. In some embodiments, a tether 30 may provide further functionality. As a few non-limiting examples, a tether 30 may enable manipulation of the exoskeleton device 10 once it has been introduced into a subject's body, the communication of liquids into and/or out of the subject's body, and/or the communication of electrical signals between the exoskeleton device 10 within the subject's body and one or more apparatuses outside of the subject's body.

In some embodiments, the tether 30 may comprise a single elongated element with a distal end that is secured to a proximal end 20p of the body 20. In other embodiments, the tether 30 may comprise a proximal extension of one or more external elements 22 of the body 20 of the exoskeleton device 10.

Figure 2:
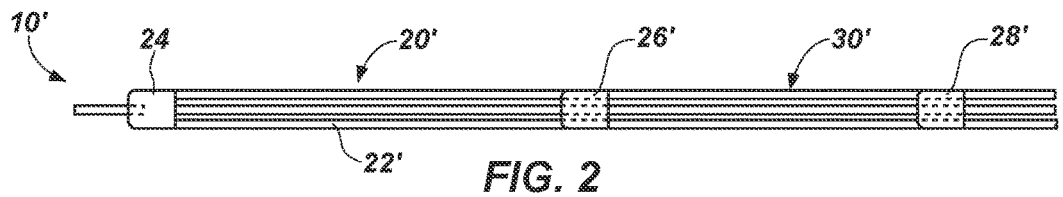
Figure 2A:
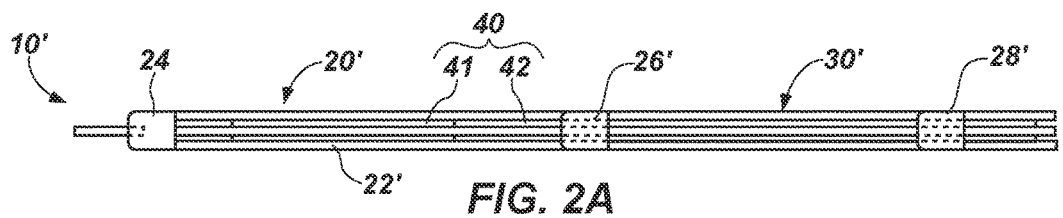

Turning now to FIGS. 2 and 2A, an embodiment of exoskeleton device 10' is illustrated that includes a body 20' that resembles the body 20 of the embodiment of exoskeleton device 10 depicted by FIGS. 1-1B, but differs from the exoskeleton device 10 in a number of respects.

As one example, the exoskeleton device 10' shown in FIGS. 2 and 2A includes a tether 30' formed by proximal extensions of at least two external elements 22'. Thus, the tether 30' includes more than one element, or it could be said that the exoskeleton device 10' includes more than one tether 30'.

As another example, the body 20' of an exoskeleton device 10' may include a proximal collar 26' that holds intermediate portions 22i' of external elements 22' in place relative to one another to define a proximal end 20p' of the body 20', with or without holding the body 20' in place relative to a proximal side of the distal portion 41 of an elongated medical instrument 40 (FIG. 2A).

As another option, a proximal collar 26' of the body 20' of an exoskeleton device 10' may be configured to slide along the lengths of the external elements 22' in a manner that enables the body 20' to accommodate and receive a distal portion 41 of an elongated medical instrument 40 (FIG. 2A). Such a proximal collar 26' may also be configured to lock into place at a desired location along the lengths of the external elements 22' to enable the proximal collar 26' to impart the body 20' with a length that corresponds to the length of the distal portion 41 and to engage a proximal end of the distal portion 41, thereby securing the body 20' in place over the distal portion 41 of the elongated medical instrument 40.

An exoskeleton device 10' may also include one or more positioning collars 28' that are located proximal to the body 20'. Each positioning collar 28' may hold the elements of a tether 30' in place relative to one another and/or hold a tether 30' in place relative to another feature, such as a proximal portion 42 of the elongated medical instrument 40.

Figure 3:
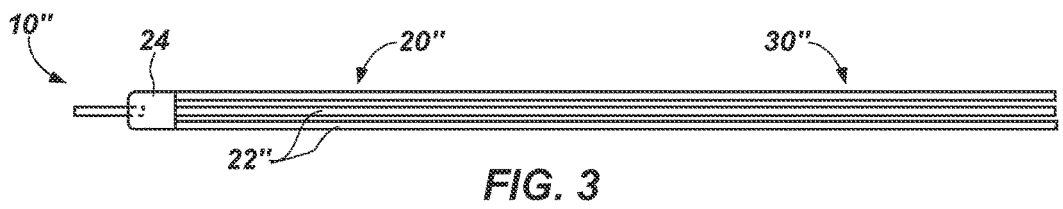
Figure 3A:
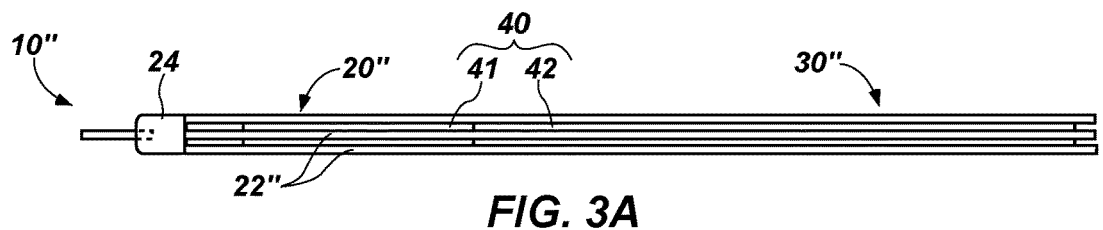
Figure 3B:
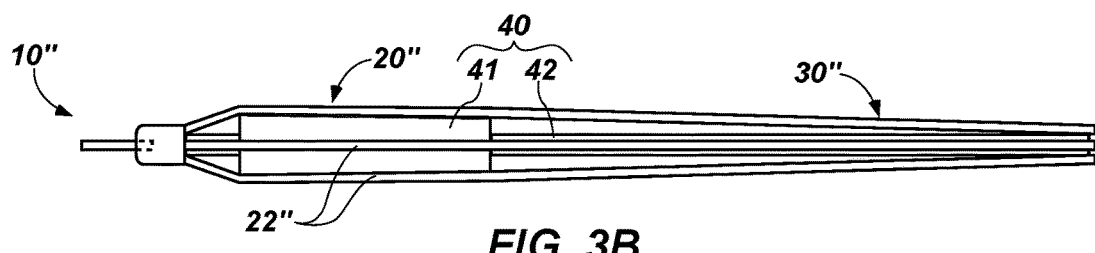

FIGS. 3-3B depict another embodiment of exoskeleton device 10'', in which each external element 22'' includes a distal portion 22d'' and a proximal portion 22p''. The distal portion 22d'' of each external element 22'' may be configured to be positioned over a distal portion 41 of an elongated medical instrument 40 with which the exoskeleton device 10'' is configured to be used. The proximal portion 22p'' of each external element 22'' may be configured to extend proximally to a location near, at or beyond a proximal end (not shown) of the elongated medical instrument 40. Thus, the proximal portion 22p'' of each external element 22'' may act as a tether 30'', or proximal portions 22p'' of a plurality of external elements 22'' may collectively function as a tether 30''. While the exoskeleton device 10'' shown in FIGS. 3-3B includes a distal collar 24, which may secure the exoskeleton device 10'' and its external elements 22'' in place at or near a distal end of the elongated medical instrument 40, the exoskeleton device 10'' may lack a proximal collar 26.

Turning now to FIGS. 4A-6C, various embodiments of another type of exoskeleton device are illustrated.

Figure 4A:
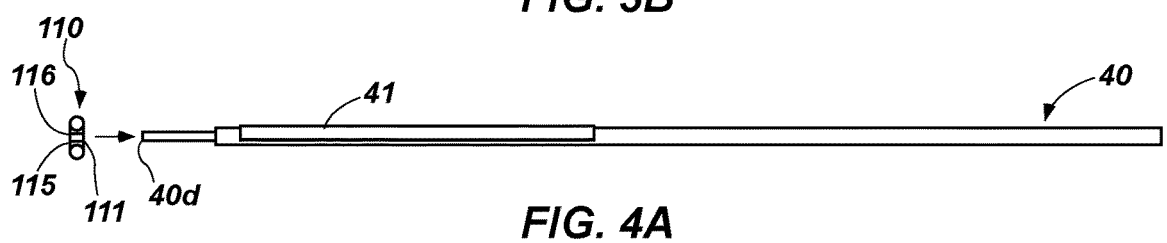
FIGS. 4A, 4B and 4C illustrate an embodiment of a body of an exoskeleton device that is in maintained in a rolled configuration before it is installed on an elongated medical instrument, as well as an embodiment of installation of the exoskeleton device onto an elongated medical instrument, which includes unrolling the body onto the elongated medical instrument in a proximal direction.
Figure 4B:
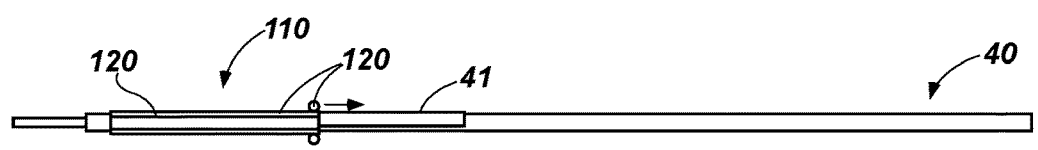
Figure 4C:
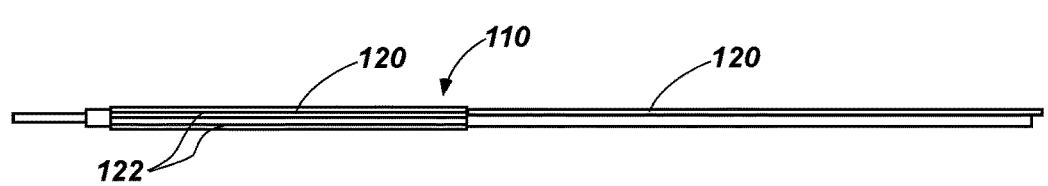

FIGS. 4A-4C show an embodiment of exoskeleton device 110 that is initially provided to a healthcare provider in a rolled configuration, as shown in FIG. 4A. In the rolled configuration, a body 120 of the exoskeleton device 110 (which may have a tubular configuration when unrolled (see, e.g., FIG. 4C)) may be circumferentially or axially rolled upon itself. While in the rolled configuration, the exoskeleton device 110 may resemble a ring with an aperture, or a lumen 111, through its center. In some embodiments, an introduction element 115, which be annular or tubular in shape and may be somewhat rigid (e.g., relative to the exoskeleton device 110 while in its rolled configuration, etc.), may be aligned with and disposed in the lumen 111. The introduction element 115 may include a lumen 116 with an inner diameter that is larger than an outer diameter or a portion of an elongated medical instrument 40 onto which the exoskeleton device 110, in its rolled configuration, is to be installed.

While in its rolled configuration, the exoskeleton device 110 is oriented relative to an elongated medical instrument 40. More specifically, the exoskeleton device 110 may be oriented such that it can be unrolled onto the elongated medical instrument 40 in a proximal direction. With the exoskeleton device 110 properly oriented, it may be positioned over a distal end 40d of the elongated medical instrument 40 and onto the elongated medical instrument 40 at a location distally adjacent to distal side of a distal portion 41 of the elongated medical instrument 40 or at the distal side of the distal portion 41. Stated another way, the distal end 40d of the elongated medical instrument 40 may be inserted into and, optionally, at least partially through a lumen 111 of the exoskeleton device 110 while the exoskeleton device 110 remains in its rolled configuration. In embodiments where the exoskeleton device 110 is rolled onto an introduction element 115, introduction of the distal end 40d of the elongated medical instrument 40 may be inserted into and, optionally, at least partially through the lumen 111 of the exoskeleton device 110 may include introducing the distal end 40d into and, optionally, at least partially through the lumen 116 of the introduction element 115.

As illustrated by FIG. 4B, once the exoskeleton device 110, in its rolled configuration, has been properly positioned on the elongated medical instrument 40, it may be unrolled in a proximal direction onto the distal portion 41 of the elongated medical instrument 40. In embodiments where the exoskeleton device 110 was rolled onto an introduction element 115, the introduction element 115 may remain in place, or it may be removed from between the exoskeleton device 110 and the elongated medical instrument 40.

FIG. 4C shows the exoskeleton device 110 in an installed configuration. A body 120 of the exoskeleton device 110, which may comprise an elastic material, may engage an outer surface of the distal portion 41 of the elongated medical instrument 40 as the exoskeleton device 110 and, more specifically, its body 120 are unrolled onto the distal portion 41. Depending on the extent to which the body 120 engages the distal portion 110, some embodiments of the exoskeleton device 110 may lack a tether. The embodiment of exoskeleton device 110 illustrated by FIGS. 4A-4C may, however, include a tether 130, which may enable manipulation of the exoskeleton device 110 once it has been introduced into a subject's body, the communication of electrical signals between the exoskeleton device 110 within the subject's body and one or more apparatuses outside of the subject's body, and/or the communication of liquids into and/or out of the subject's body.

In addition to the body 120 and an optional tether 130, an exoskeleton device 110 may include one or more external elements 122. Each external element 122 may comprise an element that has been secured to an exterior surface of the body 120, an element that has been at least partially embedded within the body 120 or an element that has been defined in the body 120 (e.g., by processes, such as extrusion, molding, etc., used to make the body 120; etc.). Any external element(s) 122 and/or tether 130 may be rolled with the body 120 of the exoskeleton device 110 when the exoskeleton device 110 is in its rolled configuration, and may unroll with the body 120 as the exoskeleton device 110 is installed on a distal portion 41 of an elongated medical instrument 40.

Figure 5A:
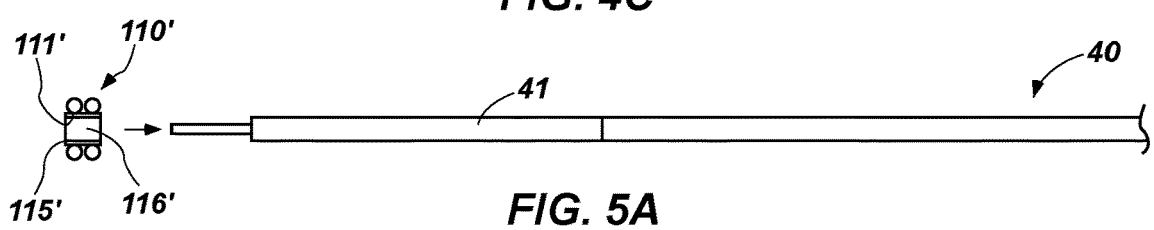
FIGS. 5A, 5B and 5C show an embodiment of a body of an exoskeleton device that is maintained in a dual rolled configuration before it is installed on an elongated medical instrument, as well as an embodiment of installation of the exoskeleton device onto an elongated medical instrument, which includes unrolling a distal side of the body in a distal direction and unrolling a proximal side of the body in a proximal direction.
Figure 5B:
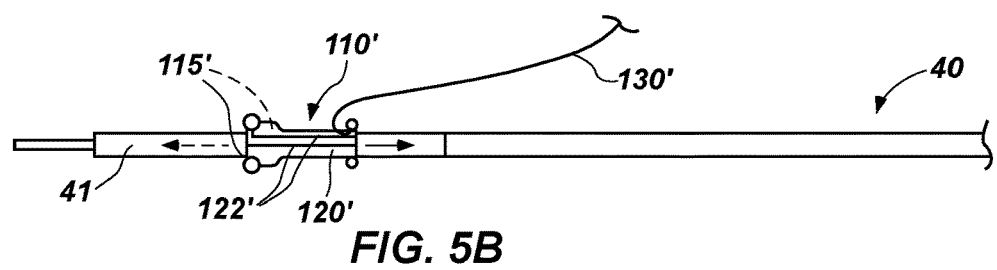
Figure 5C:
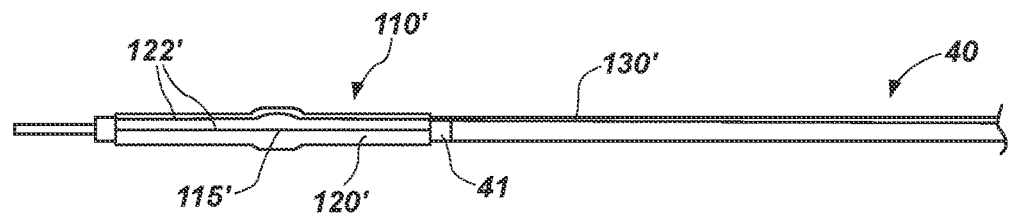

Looking now to FIGS. 5A-5C, another embodiment of exoskeleton device 110' is depicted. In its initial configuration (i.e., the configuration in which the exoskeleton device 110' is provided to a healthcare professional), which is shown in FIG. 5A, both ends of the exoskeleton device 110' are rolled toward a center of the length of the exoskeleton device 110', imparting the exoskeleton device 110' with the dual rolled configuration shown in FIG. 5A. An introduction element 115', which may be configured in the same manner as or in a similar manner to the introduction element 115 shown in FIG. 4A, may extend through a lumen 111' of the dual rolled configuration of the exoskeleton device 110', may facilitate its introduction onto an elongated medical instrument 40.

After the exoskeleton device 110', in its rolled configuration, has been properly positioned on the elongated medical instrument 40, its two sides, or rolls, may be unrolled onto the distal portion 41 of the elongated medical instrument 40 in their respective proximal and distal directions. The introduction element 115', if any, may remain in place, or it may be removed after one side of the exoskeleton device 110' has been at least partially unrolled, but while the other side of the exoskeleton device 110' remains rolled (i.e., while the introduction element 115' is still accessible).

FIG. 5C shows the exoskeleton device 110' in an installed configuration, in which its elongated body 120', one or more optional external elements 122' and an optional tether 130' can be seen, each of which may be configured in the same manner as or in a similar manner to the corresponding elements described in reference to FIGS. 4A-4C.

Figure 6A:
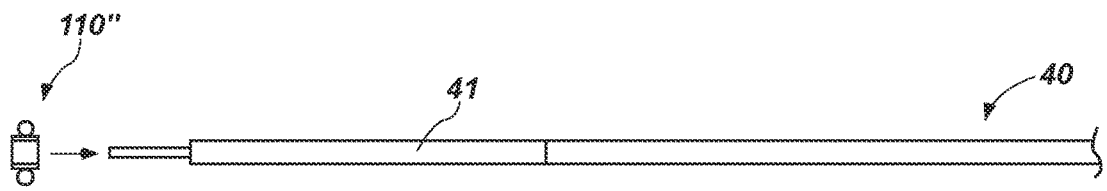
FIGS. 6A, 6B and 6C depict another embodiment of a body of an exoskeleton device that is maintained in a rolled configuration before it is installed on an elongated medical instrument, as well as an embodiment of installation of the exoskeleton device onto an elongated medical instrument, which includes unrolling the body in a distal direction.
Figure 6B:
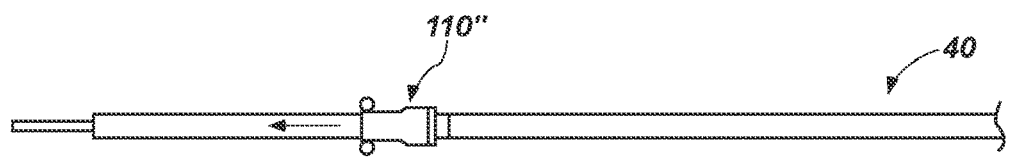
Figure 6C:
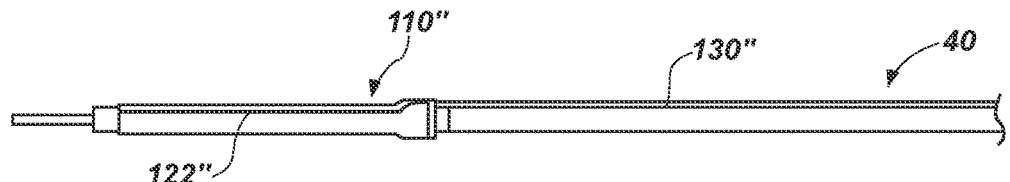

FIGS. 6A-6C illustrate an embodiment of exoskeleton device 110" having a configuration similar to that of the embodiment of exoskeleton device 110 shown in FIGS. 4A-4C, but rolled from a direction that facilitates unrolling in a distal direction (as shown in FIG. 6B). As such, as illustrated by FIGS. 6A and 6B, proximal portions of any external elements 122" and a tether 130", if any, may extend from a proximal side of the rolled configuration of the exoskeleton device 110" without having been rolled up themselves.

In various embodiments, the body of an exoskeleton device, or at least a portion of the body, may comprise a material that shrinks when exposed to certain conditions (e.g., an elevated temperature, etc.). The body of such an exoskeleton device may be introduced onto an elongated medical instrument at a desired location, and then shrunk to a size that enables the body of the exoskeleton device to engage the elongated medical instrument.

With reference turned to FIGS. 1, 7A, 7B and 8, a variety of optional functions that may be performed by the external elements 22 (or external elements 22', 22", 122, 122', 122"—FIGS. 2, 3, 4A, 5A and 6A, respectively) of an exoskeleton device 10, 10', 10", 110, 110', 110" (FIGS. 1, 2, 3, 4A, 5A and 6A, respectively) will now be described.

With reference to FIG. 1, various embodiments of external elements 22 include, but are not limited to, wires, elongated polymeric elements (which may expand when placed under a load and resiliently contract when the load is released; more specifically, a width of a polymeric element may expand when placed under tensile stress and resiliently contract when the tensile stress is released) and hypotubes. In some embodiments, the external elements 22 may include edges that enable them to engage an adjacent object, such as an arterial plaque. Such an edge may comprise blade, or arthrotome, which may enable the external elements 22 to score or cut into an adjacent object. For example, as shown in FIGS. 1A-1, when the body 20 of the exoskeleton device 10 is in a relaxed state, an edge 22e of each external element 22 carried by the body 20 may be oriented radially or substantially radially relative to a longitudinal axis of the external element 22. As an expandable element (e.g., a balloon etc.) of an elongated medical instrument 40 over which the exoskeleton device 10 has been placed expands and causes the body 20 of the exoskeleton device 10 circumferentially expand, as shown in FIGS. 1B-1, the angles at which the edges 22e of the external elements 22 are oriented relative to the body 20 may become more tangential.

Figure 7A:
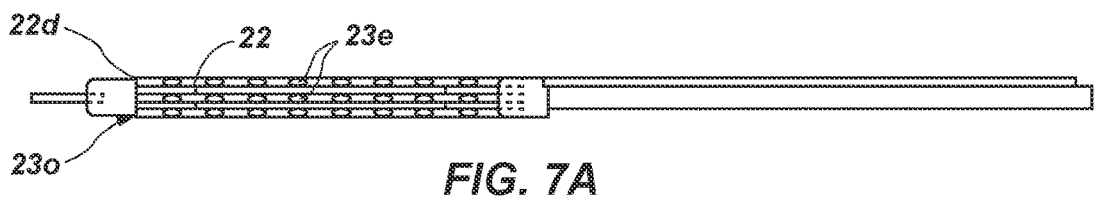
FIGS. 7A and 7B show an embodiment of an exoskeleton device with external elements that are configured to enable fluids to be conveyed through the exoskeleton device to one or more locations within a subject's body and/or from one or more locations within the subject's body.
Figure 7B:
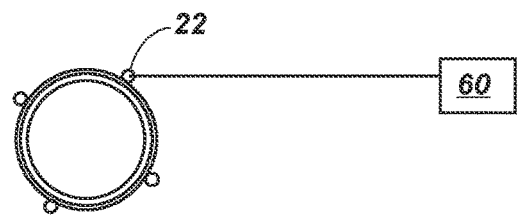

As inferred by the potential use of hypotubes to define external elements 22, an external element 22 may, as another option, include a conduit (not shown) extending along its length. As an alternative to the use of a hypotube, an elongated polymeric element may include a conduit. An external element 22 with a conduit may be configured to convey, or communicate, fluid from one location to another (e.g., from a location outside of a subject's body to the location of the external element 22, etc.). Thus, an external element 22 that includes a conduit may also include one or more pores 23p or other openings along its length, as illustrated by FIGS. 7A and 7B. In addition, or as an alternative, a distal end of the conduit may terminate at an opening 23o, which may be located along the length of an external element 22 or at a distal end 22d of the external element 22. In embodiments where the conduit and its associated pores 23p and/or opening(s) 23o communicate liquid to a desired location within a subject's body, the liquid may be forced from an external source 50 into the conduit and out of the pores 23p and/or opening(s) 23o. In embodiments where the pores 23p and/or opening(s) 23o are used to obtain a sample from a subject's body, a collection element (not shown) located outside of the subject's body may create or be associated with a vacuum source to apply a vacuum to the conduit and its associated pores 23p and/or opening(s) 23o.

As another option, and with continued reference to FIGS. 7A and 7B, one or more of the external elements 22 may comprise wires. The wires may comprise standalone electrically conductive wires or substrate (e.g., a flexible substrate, a circuit board, etc.) that carries one or more electrically conductive elements. In embodiments where one or more external elements 22 comprise such circuitry, the circuitry may be configured to convey electricity with minimal resistance, it may comprise one or more electrically resistive (i.e., heating) elements. In embodiments where an external element 22 comprises circuitry, the circuitry may communicate with an electronic device 60 located outside of a subject's body and, in some embodiments, with one or more electronic components 22e (e.g., electrodes, sensors, thermistors, etc.) carried by the exoskeleton device 10.

An external element 22 that comprises a wire or a similar structure may be configured to shape an elongated medical instrument 40 on which the exoskeleton device 10 of which the external element 22 is a part is disposed. In such an embodiment, the external element 22 may be configured to hold a shape into which it is formed (e.g., it may be malleable, etc.); Alternatively, the external element 22 may be flexible under certain conditions (e.g., at room temperature, etc.) and more rigidly hold a desired shape under other conditions (e.g., at body temperature) (e.g., it may comprise a shape memory alloy, such as a nitinol (Nickel Titanium Naval Ordinance Laboratory) material; etc.). Such an embodiment of external element 22 may enable a healthcare professional to impart a flexible elongated medical instrument 40 (e.g., a catheter, etc.) with a desired shape when the elongated medical instrument 40 is introduced into a subject's body or after the elongated medical instrument 40 has been introduced into the subject's body.

Figure 8:
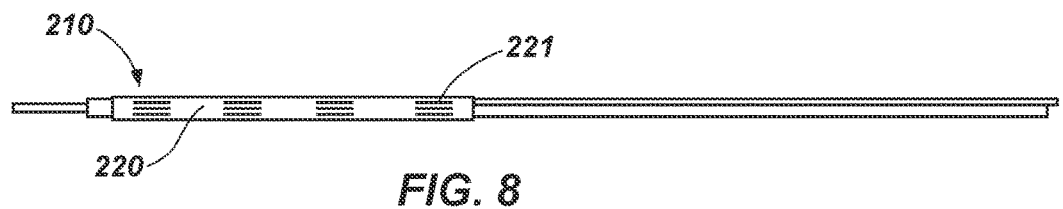
FIG. 8 depicts an embodiment of exoskeleton device with a body that is configured to hold and deliver a substance (e.g., a therapeutic agent in a liquid state or a solid state, a medicament in a liquid state or a solid state, etc.) to a desired location within a body of a subject.

FIG. 8 illustrates an embodiment of an exoskeleton device 210 with a body 220 that may carry a substance 221 that is to be delivered to a location within a subject's body. The body 220 of the exoskeleton device 210 may comprise a matrix that carries the substance 221 that is to be delivered into the subject's body. In a specific embodiment, the body 220 may have an open celled porous structure, which may impart it with sponge-like characteristics. The matrix of the body 220 may be formed from any of a variety of suitable materials, including, without limitation, polyethylene, latex, etc. In some embodiments, the body 220 may include an absorbent material, such as a hydrogel or the like.

The substance 221 absorbed by the body 220 of the exoskeleton device 210 may comprise a therapeutic agent, medicament, a dye or any other substance a healthcare professional may want to introduce into a subject's body, and it may be in a solid form or a liquid form. The substance 221 may be integrated into the matrix of the body 220 of the exoskeleton device 210 as the body 220 is formed, after the body 220 is formed but before it is packaged or by the healthcare professional. Alternatively, the substance 221 may be added directly to the body 220 of the exoskeleton device 210 by a healthcare professional. As another option, the substance 221 may be introduced into the body 220 of the exoskeleton device 210 through a tether 230 that communicates with the body 220 (e.g., from a location outside the subject's body while the exoskeleton device 210 resides within the subject's body, etc.).

An exoskeleton device 210 of the type described in reference to FIG. 8 may be configured to obtain a sample from a location within a body of a subject. When the exoskeleton device 210 is positioned at a desired location within a subject's body, the body 220 of such an exoskeleton device 210 may absorb a liquid or a fluid, or to receive another material from within the subject's body.

In an embodiment of use of an exoskeleton device, reference is returned to FIGS. 3-3B of the drawings. As illustrated by FIG. 3, an exoskeleton device 10" may be provided. The exoskeleton device 10" may be installed onto an appropriate location of an elongated medical instrument 40 (e.g., onto an exterior of the elongated medical instrument 40, etc.), as shown in FIG. 3A. As depicted, the exoskeleton device 10" may be installed on a distal portion 41 of an elongated medical instrument 40. In the specific embodiment depicted by FIG. 3A, the exoskeleton device 10" may be installed over an angioplasty balloon of an angioplasty device.

With the exoskeleton device 10" in place upon the elongated medical instrument 40, the elongated medical instrument 40 and the exoskeleton device 10" may be introduced into a body of a subject, and introduced to a desired location within the subject's body. In embodiments where the elongated medical instrument 40 comprises an angioplasty device, the angioplasty balloon of such a device and the exoskeleton device 10" carried thereby may be introduced into a blood vessel and advanced to a location where a plaque at least partially blocks the flow of blood through the blood vessel.

With the elongated medical instrument 40 and the exoskeleton device 10" properly positioned within the subject's body, one or both of the exoskeleton device 10" and the elongated medical instrument 40 may be used to perform a procedure at the desired location. Continuing with the embodiment where the elongated medical instrument 40 is an angioplasty device and its distal portion 41 comprises an angioplasty balloon, the angioplasty balloon of the angioplasty device may be inflated. Inflation of the angioplasty balloon may cause external elements 22" of the exoskeleton device 10" to contact the plaque, and even to engage the plaque. In embodiments where the external elements 22" comprise blades, the external elements 22" may cut into the plaque.

With the exoskeleton device 10" and its external elements 22", if any, in place, the exoskeleton device 10" may be used to perform a procedure at the desired location. As a non-limiting example, in embodiments where the elongated medical instrument 40 and the exoskeleton device 10" are used to perform angioplasty, a tether 30" of the exoskeleton device 10" may be manipulated to cause the external elements 22" to cut into the plaque. As another example, the exoskeleton device 10" may be used to deliver a substance to the desired location, to obtain a sample from the desired location, to heat the desired location, to sense a particular condition (e.g., a temperature, etc.) at the desired location or to perform any of a variety of other functions at the desired location.

Once the desired procedure has been performed, the elongated medical instrument 40 and the exoskeleton device 10" may be removed from the subject's body.

Although the preceding disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. An exoskeleton device configured for assembly with an elongated medical instrument, the exoskeleton device comprising:
    a body positionable over an entirety of an expandable element of the elongated medical instrument and capable of enabling removal of the expandable element from the body, the body including at least one blade that:
    is elongated;

is capable of being positioned at a radial position around a circumference of the expandable element of the elongated medical instrument; and includes a scoring edge that extends along a length of the at least one blade with a tangential-radial orientation that changes relative to a longitudinal axis of the at least one blade while the body circumferentially expands.

2. The exoskeleton device of claim 1, wherein the at least one blade includes a plurality of blades capable of being positioned at different radial positions around the circumference of the elongated medical instrument, each blade of the plurality of blades including a scoring edge that extends along a length of the blade with a tangential-radial orientation that changes while the body circumferentially expands.

3. The exoskeleton device of claim 1, wherein the body is capable of:
expanding when the expandable element of the elongated medical instrument is expanded; and
following use of the exoskeleton device, resiliently retracting when the expandable element of the elongated medical instrument is retracted from its expanded state.

4. The exoskeleton device of claim 1, wherein the at least one blade comprises an elongated polymer element.

5. The exoskeleton device of claim 1, wherein the at least one blade comprises a conduit.

6. The exoskeleton device of claim 5, wherein the body comprises a hypotube.

7. The exoskeleton device of claim 5, wherein the at least one blade includes at least one opening at a distal end of the conduit.

8. The exoskeleton device of claim 1, wherein the at least one blade includes at least one pore therethrough to enable fluid to flow to an exterior surface of the body.

9. The exoskeleton device of claim 1, further comprising:
a proximal portion capable of extending substantially to a proximal end of the elongated medical instrument.

10. An exoskeleton device for use with an elongated medical instrument, comprising:
a body positionable over and removable from an expandable element of the elongated medical instrument, the body comprising an elongated tubular element capable of substantially surrounding the expandable element of the elongated medical instrument and of circumferentially expanding upon expanding the expandable element of the elongated medical instrument and resiliently circumferentially contracting following use of the exoskeleton device and retraction of the expandable element from its expanded state,
the body including a plurality of blades:
each blade of the plurality of blades comprising an elongated element;
being positioned at different radial positions around a circumference of the body; and
each blade of the plurality of blades including a scoring edge that extends along a length of the blade with a tangential-radial orientation that changes relative to a longitudinal axis of the blade while the body circumferentially expands.

11. The exoskeleton device of claim 10, wherein each scoring edge comprises a cutting edge.

12. The exoskeleton device of claim 10, wherein the body has a contracted state in which the body can engage an unexpanded portion of the elongated medical instrument.

13. The exoskeleton device of claim 10, wherein the body is capable of being used with elongated medical instruments of a plurality of different diameters.

14. The exoskeleton device of claim 10, wherein the body is capable of absorbing a therapeutic agent, a medicament or another liquid.

15. The exoskeleton device of claim 10, wherein the body carries a therapeutic agent or a medicament.

16. The exoskeleton device of claim 10, further comprising:
a proximal portion capable of extending substantially to a proximal end of the elongated medical instrument.

* * * * *